United States Patent [19]

Rossi

[11] Patent Number: 4,541,107
[45] Date of Patent: Sep. 10, 1985

[54] MOVING X-RAY MASK WITH SPIRAL WINDOW

[75] Inventor: Remo J. Rossi, Billerica, Mass.

[73] Assignee: John K. Grady, Littleton, Mass.

[21] Appl. No.: 617,312

[22] Filed: Jun. 4, 1984

[51] Int. Cl.³ .......................... G01T 1/20; G01T 1/00; G01J 1/42
[52] U.S. Cl. ...................................... 378/146; 378/44; 378/99
[58] Field of Search ................. 430/5; 378/35, 44, 99, 378/146

[56] References Cited

U.S. PATENT DOCUMENTS 4,315,146  2/1982  Rudin ................................. 378/146

Primary Examiner—Richard L. Schilling
Attorney, Agent, or Firm—James H. Grover

[57] ABSTRACT

An X-ray system includes an X-ray source directing X-radiation on a first path through a subject to an X-radiation receptor which responds to X-rays to direct light radiation on a secondary path to a light image plane. In either path or both paths is a rotating radiation-opaque mask having one or more spiral radio-transparent windows which sweep through the path as the mask rotates. Each spiral window may be formed by the overlap of coaxial spiral windows in superimposed masks which are relatively adjustable in phase to vary the window width.

19 Claims, 5 Drawing Figures

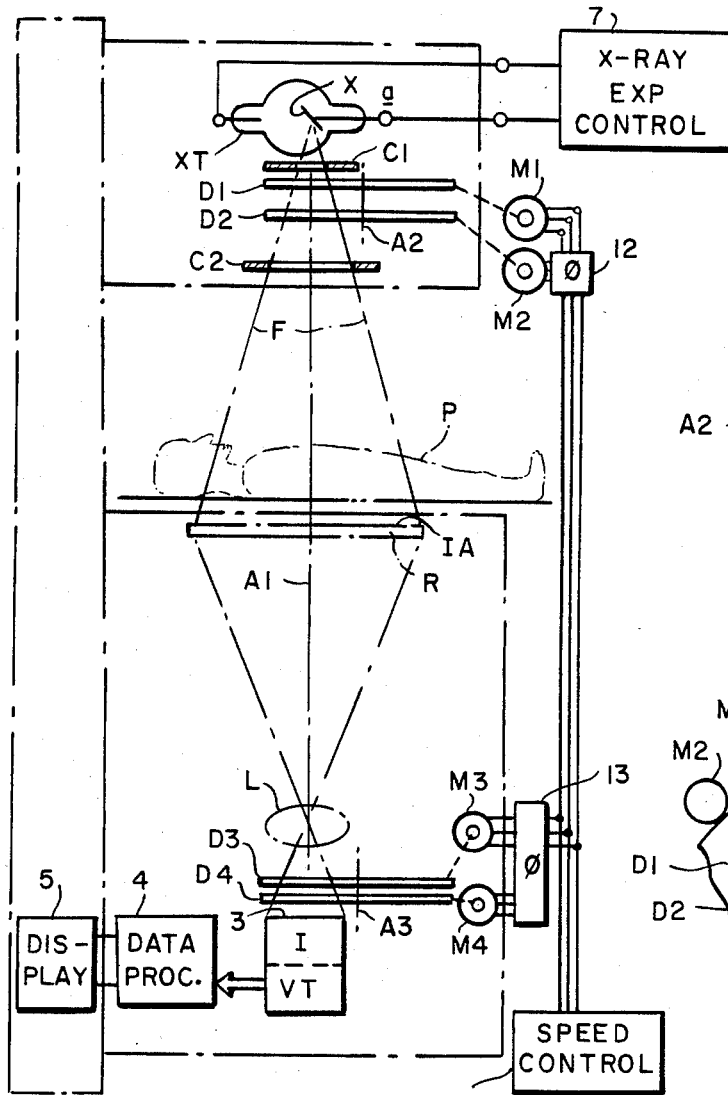
FIG.1
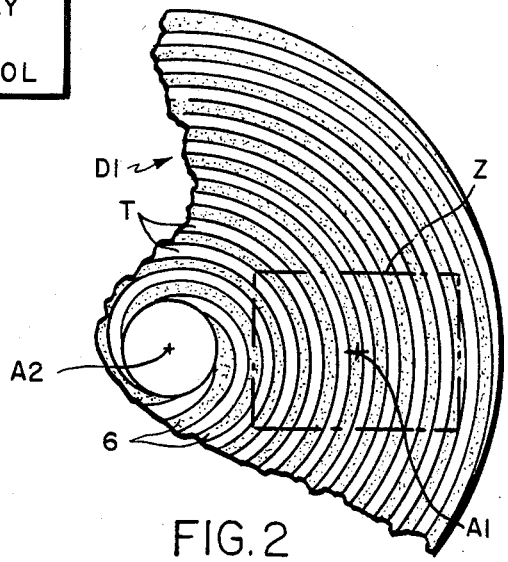
FIG.2
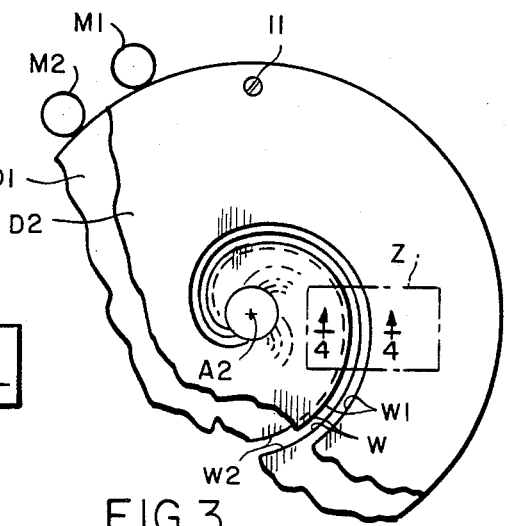
FIG.3
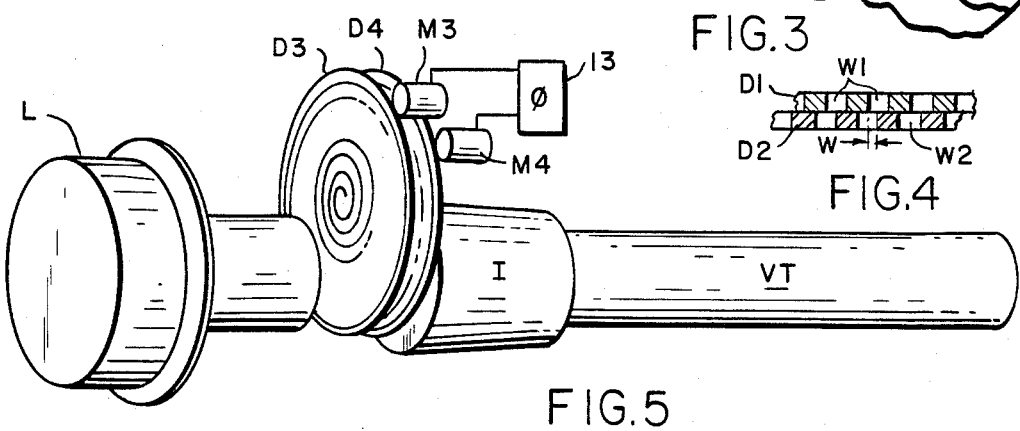
FIG.4
FIG.5

MOVING X-RAY MASK WITH SPIRAL WINDOW

BACKGROUND OF THE INVENTION

In X-ray examination of a subject such as a human patient an ideal radiographic image is formed by a point X-ray source projected on a straight line through the subject to an X-ray receptor such as radiographic film or a fluoroscopic screen. In practice the cathode of an X-ray tube is not a perfect point source, and some X-rays are scattered from parts of the subject to areas of the image where they represent radiological noise rather than a true shadow of the subject. X-ray scatter can be reduced and the quality of the image on the receptor can be improved by interposing between the X-ray source and X-ray receptor a moving radio-opaque mask with a narrow, elongate radio-transparent window which casts a moving fan shaped X-ray scanning beam through the subject. X-rays scattered from the subject are further reduced by similar coordinated, moving X-ray masks between the subject and the film as described in U.S. Pat. No. 4,315,146. To be effective the X-ray-opaque masks must be a very heavy metal such as lead and therefore are usually in the shape of rotating disks. Experimental techniques for adjusting the window width, such as described in *Radiology*, 120: 705–711, September 1976, are not applicable to disks, but in most radiological examination adjustment of the window is needed.

Accordingly the object of the present invention is to provide a form of rotating X-ray masking disk with a window of uniform width throughout its length, as compared to the sectoral windows of previous disk masks. A further object is to provide an improved way of adjusting the width of the windows.

SUMMARY OF THE INVENTION

An X-ray system for radiological examination of a subject comprises an X-ray source directing radiation on a first path through a subject position; an X-radiation receptor on the path beyond the subject responsive to received X-rays to direct light radiation on a secondary path to a light image plane; and a rotating radiation-opaque mask in at least one of said paths including a spiral radio-transparent window sweeping through the path as the mask rotates.

DRAWING

FIG. 1 is a general schematic view of X-ray system with moving radiation masks having spiral windows;

FIG. 2 is a fragmentary plan view of a mask with spiral windows;

FIG. 3 is a fragmentary plan view of a composite, adjustable mask;

FIG. 4 is a section on line 4—4 of FIG. 3; and

FIG. 5 is an isometric view of a portion of the system of FIG. 1.

DESCRIPTION

In the X-ray system of FIG. 1 the X-radiation source is the focal spot X on the anode a of an X-ray tube XT. The X-ray tube is energized by an electronic X-ray exposure control 1. From the source X a pyramidal or conical beam is directed along a radiation path on an axis A1 toward the position P of a human patient subject on an X-ray support table T. The beam is defined by X-ray-opaque collimators C1 and C2 and further restricted to a fan shaped beam F by a composite X-ray opaque mask formed by two disks D1 and D2 rotating on an axis A2 and which are the subject of the present invention.

The fan shaped X-ray beam F passes through the subject position P to an X-ray receptor R having an X-ray responsive image area or plane IA. Typically the receptor is a scintillation screen emitting visible light as secondary radiation corresponding to the received X-ray shadow image, and directed by a lens system L on a secondary, light-radiation path to the light image plane 3 of an electro-optical video system I, VT which converts the light image into electrical video signals. The video signals are applied through a data processor 4 to a display 5. Between the lens system L and light image plane 3 is a light mask consisting of two light-opaque disks D3 and D4 similar to the X-ray-opaque disks D1 and D2, and rotating on an axis A3.

The X-ray-opaque disks D1 and D2 are partially composed of a body 6 of heavy metal such as lead or uranium (shown shaded) bonded to spiral windows 7 of radio-transparent material such as epoxy with sufficient structural strength to support the spaced spiral turns of heavy metal. Preferably each radio-transparent window is of uniform width along its spiral and spacing radially from the axis A2 of rotation of the mask D1, D2. As shown in FIG. 2 each disk has a plurality of windows with 360° turns, but, as shown in FIG. 3, each disk may have a single spiral window 7, and the spiral may be more or less than 360°. It is preferred that the spiral windows 7 be coaxial and spaced apart by radio-opaque spirals 6 the same distance as the window width. The spirals of respective disks are equivalent geometrically. A single disk D1 with a single spiral window driven by one motor M1 may be used, but will not allow for adjustment of the window width.

As shown in FIGS. 3 and 4 either the X-ray mask D1, D2 or light mask D3, D4, or both, may be composite, formed by two disks closely spaced in substantial, sliding contact (FIG. 4). In each composite mask the respective disks D1, D2 or D3, D4 of each pair have coaxial spiral, radio-transparent windows W1 and W2 which overlap each to form an effective window W smaller than either of the overlapping windows except in the one instance of register.

The overlap of respective disk windows of either pair of masks D1, D2 or D3, D4, can be adjusted to vary the smaller effective window W by shifting the angular phase relation between the spirals of the respective disks of a mask pair. This phase adjustment may be made by relative rotation of the disks and then locking the disks in adjusted relation as by a set screw 11.

But for more practical and convenient phase adjustment each pair of disks of each mask is driven respectively by pairs of motors which are phase controlled. Shown in FIG. 1 is one pair of motors M1 and M2 respectively driving disks D1 and D2; or in FIGS. 1, 3 and 5 a pair of motors M3 and M4 driving disks D3 and D4. As shown in FIG. 1 the pair of motors M1, M2 driving disks D1 and D2 are adjusted in angular relation by a phase control 12; the other pair of motors M3, M4 being adjusted in relative angle by a phase control 13. Both phase controls are supplied electrical ppwer from a speed control 14 connected to three phase power mains.

As shown by way of example in FIGS. 3 and 5 the disks of each mask pair are rim driven independently by phase controlled motors. Consequently a momentary relative speed difference of the motors and disks controls and adjusts the overlap of the disk windows and the width of the effective window W. The motor pairs M1, M2 for the X-ray-opaque disks D1, D2 and M3, M4 for the light-opaque disks D3, D4 are otherwise synchronously driven so that the effective windows of the masks are maintained in optical register.

Rotation of the effective window 7 (FIG. 2) or W (FIGS. 4 and 5) sweeps the windows radially through a zone Z across the X-ray path as shown in phantom in FIGS. 2 and 3. This zone corresponds to the subject position and the image area IA. As contrasted with prior sector window scanning disks, the spiral window disk of the present invention is of uniform width throughout its length and hence transmits a substantially uniform intensity of energy throughout its length. With multiple turns or multiple windows in each disk the rate of scan across the zone Z is increased in proportion to the number of turns and the rotational speed of the disk mask is correspondingly decreased. The more turns each for each window the closer each turn in the scanning zone Z is to parallel, and the closer each window approaches to translatory rectilinear sweep of the zone.

It should be understood that the present disclosure is for the purpose of illustration only and that this invention includes all modifications and equivalents which fall within the scope of the appended claims.

I claim:

1. An X-ray system for radiological examination of a subject comprising:
an X-ray source directing radiation on a first path through a subject position;
an X-radiation receptor on the path beyond the subject responsive to received X-rays to direct light radiation on a secondary path to a light image plane; and
a rotating radiation-opaque mask in one of said paths including a spiral radio-transparent window sweeping through the path as the mask rotates.

2. A system according to claim 1 wherein the mask is X-ray opaque.

3. A system according to claim 1 wherein the mask is light opaque.

4. A system according to claim 1 wherein the window is of uniform width along its spiral.

5. A system according to claim 1 wherein the window is of uniform width radially of the axis of rotation of the mask.

6. A system according to claim 1 wherein the spiral window has a plurality of 360° turns.

7. A system according to claim 1 wherein the mask has a plurality of spaced, coaxial, spiral windows.

8. A system according to claim 7 wherein the windows are uniformly spaced.

9. A system according to claim 7 wherein the windows are spirally equal.

10. A system according to claim 7 wherein the windows are equal in width.

11. A system according to claim 10 wherein the windows are spaced apart at least their width.

12. A system according to claim 1 wherein the mask comprises two closely superimposed, coaxial radio-opaque disks, respective disks having coaxial spiral, radio-transparent windows, disposed to overlap one another to define a smaller effective window.

13. A system according to claim 12 in combination with drive means for rotating the disks to sweep the effective windows through the X-ray path.

14. A combination according to claim 13 wherein the drive means includes phasing means for adjusting the overlap of the windows.

15. A combination according to claim 13 wherein the drive means is separately coupled to respective disks and includes means to adjust the phase relation of the disks and hence the overlap of their windows.

16. A combination according to claim 13 wherein the drive means comprises two motors respectively driving the disks and a control of the relative phase of the motors.

17. In an X-ray system directing X-radiation on a path through a subject position to an X-ray receptor emitting secondary, light radiation a scatter reducing device comprising:
two closely superimposed, coaxial radio-opaque disks, respective disks having coaxial spiral, radio transparent windows, disposed to overlap one another to define a smaller effective window; and
means rotatively supporting the disks.

18. A device according to claim 17 including means for adjusting the degree of overlap of the windows.

19. A device according to claim 17 wherein the disks are X-ray opaque.

* * * * *